US010080531B2

(12) United States Patent
Miller et al.

(10) Patent No.: US 10,080,531 B2
(45) Date of Patent: Sep. 25, 2018

(54) TRAUMATIC INJURY SELF-TREATMENT AND MEDICAL INFORMATION APPARATUS AND RELATED METHODS

(71) Applicant: The United States of America as represented by the Secretary of the Navy, Washington, DC (US)

(72) Inventors: Gerry Miller, Bedford, IN (US); Garry Wieneke, Montgomery, IN (US); Ameer Beitvashahi, Bloomington, IN (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 358 days.

(21) Appl. No.: 15/134,696

(22) Filed: Apr. 21, 2016

(65) Prior Publication Data

US 2017/0035369 A1 Feb. 9, 2017

Related U.S. Application Data

(60) Provisional application No. 62/202,315, filed on Aug. 7, 2015.

(51) Int. Cl.
*A61B 17/132* (2006.01)
*A61B 5/00* (2006.01)
(Continued)

(52) U.S. Cl.
CPC .......... *A61B 5/747* (2013.01); *A61B 5/02438* (2013.01); *A61B 5/1112* (2013.01);
(Continued)

(58) Field of Classification Search
CPC ... A61B 5/747; A61B 17/1322; A61B 5/7445; A61B 5/1112; A61B 5/02438; A61B 2017/00044; A61B 5/0022; G01S 19/42; A61M 5/002; A61M 2005/2013; A61M 5/20
See application file for complete search history.

(56) References Cited

U.S. PATENT DOCUMENTS 6,654,987 B1 12/2003 Wu
8,065,781 B2 11/2011 Chao
(Continued)

*Primary Examiner* — Katherine M Shi
*Assistant Examiner* — Michael Mendoza
(74) *Attorney, Agent, or Firm* — Christopher A. Monsey

(57) ABSTRACT

Embodiments of medical device(s) configured for use by a debilitated or single handed user including flexible strap sections, a semi-rigid strap section configured to be formed into at least a partially enclosing semi-rigid shape by the user, and a ratcheting strap retraction unit or buckle coupled to one end of the first flexible strap section and an oversized buckle on an opposing end of the first strap section. A semi-rigid strap section is configured to insert into and be drawn into the oversized buckle and formed into an enclosing shape, maneuvered by the user over an injured appendage past a point of injury, then folded back over the oversized buckle; next the user operates the ratcheting strap retraction unit or buckle to constrict the strap sections to apply enclosing pressure to the injured appendage. Embodiments can further comprise an injector medical case module and a medical condition monitoring system.

8 Claims, 8 Drawing Sheets

(51) Int. Cl.
*A61M 5/00* (2006.01)
*A61B 5/024* (2006.01)
*A61B 5/11* (2006.01)
*G01S 19/42* (2010.01)
*A61M 5/20* (2006.01)
*A61B 17/00* (2006.01)

(52) U.S. Cl.
CPC ........ *A61B 5/7445* (2013.01); *A61B 17/1322* (2013.01); *A61M 5/002* (2013.01); *G01S 19/42* (2013.01); *A61B 5/0022* (2013.01); *A61B 2017/00044* (2013.01); *A61M 5/20* (2013.01); *A61M 2005/2013* (2013.01)

(56) References Cited

U.S. PATENT DOCUMENTS

| | | |
|---|---|---|
| 8,370,997 B2 | 2/2013 | Wright |
| 8,973,222 B2 | 3/2015 | Breeden et al. |
| 2010/0234877 A1* | 9/2010 | Pienkowski ....... A61B 17/1325 606/203 |
| 2012/0233823 A1 | 9/2012 | Chou |
| 2012/0241545 A1 | 9/2012 | Borntrager |

* cited by examiner

TRAUMATIC INJURY SELF-TREATMENT AND MEDICAL INFORMATION APPARATUS AND RELATED METHODS

CROSS-REFERENCE TO RELATED APPLICATIONS

The present application claims priority to U.S. Provisional Patent Application Ser. No. 62/202,315, filed Aug. 7, 2015, entitled "MEDICAL APPARATUS CONFIGURED TO PERMIT SOLE USE, TREAT AN INJURY, AND FACILITATE TREATMENT TO INCLUDE PROVIDING INFORMATION TO USER AND MEDICAL RESPONDERS," the disclosure of which is expressly incorporated by reference herein.

STATEMENT REGARDING FEDERALLY SPONSORED RESEARCH OR DEVELOPMENT

The invention described herein was made in the performance of official duties by employees of the Department of the Navy and may be manufactured, used and licensed by or for the United States Government for any governmental purpose without payment of any royalties thereon. This invention (Navy Case 200,268) is assigned to the United States Government and is available for licensing for commercial purposes. Licensing and technical inquiries may be directed to the Technology Transfer Office, Naval Surface Warfare Center Crane, email: Cran_CTO@navy.mil.

BACKGROUND AND SUMMARY OF THE INVENTION

The present invention relates to medical treatment systems usable by an injured party to self-treat their injuries and provide information to the injured party or user as well as other entities such as first responders. In particular, an embodiment is directed to a solo tourniquet (ST) which is adapted for use by an injured party who is likely to have reduced ability to utilize and manipulate self-treatment items or equipment due to, e.g., shock, lack of ability to grip, restriction to one-handed application of a given medical treatment apparatus, difficulty due to loss of motor skills due to, e.g., shock, blood loss, significant injury, difficulty in maneuvering one or more elements of the medical treatment equipment or items.

Various embodiments of the present disclosure provide a variety of benefits, for example, how various embodiments can be easily stowed on a carrier, and/or embedded in clothing or user's vest or pant leg. Exemplary embodiments can be constructed using a ratchet, a strap with semi-rigid or malleable wire with a non-slip rubber coating. An exemplary embodiment can further include medical modules including treatment modules and electronic modules with a display that couples with other components such as shirt and finger heart rate sensors. Embodiments of these modules can include systems for monitoring heart rate and enabling a doctor, medic or injured party/casualty/user a capacity for applying self-treatments such as a coagulant agent and clotting factors to a trauma or injury area that can be used in treatments such as prevention of bleeding hemorrhage and relief of pain.

Embodiments of the invention can include apparatus and methods optimized for use as a self-treat or "solo" one-handed self-treatment system applied by a user in an emergency. An embodiment of the invention can also monitor and store time of ST application for later retrieval. An embodiment of the invention can include sensor elements built into a uniform (e.g., undershirt) that includes sensors touching the user's skin to allow heart rate electrical signal pick up. Embodiments can include a wireless system which communicates with a remote or portable system to communicate various data such as heart rate, activation of the self-treatment system, time of activation, user identity (ID), location or bearing to user, etc.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which.

DETAILED DESCRIPTION OF THE DRAWINGS

The embodiments of the invention described herein are not intended to be exhaustive or to limit the invention to precise forms disclosed. Rather, the embodiments selected for description have been chosen to enable one skilled in the art to practice the invention.

Figure 1:
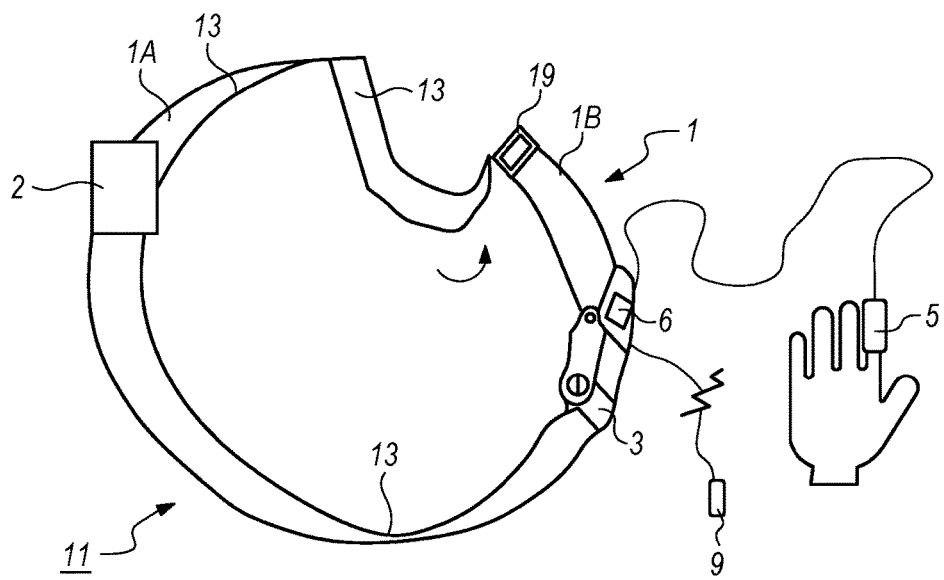
FIG. 1 shows a view of an exemplary ST with various elements of the disclosure including several medical modules, ratchet, and semi-rigid strap in accordance with one embodiment of the invention.

FIG. 1 shows a view of an exemplary ST assembly 11 with various elements of the invention including various modules 2 and 6. A user can self-treat or apply the ST assembly 11 without assistance to an injured appendage, e.g., arm, in a safer, simpler, and an easier fashion than existing options. In one exemplary embodiment, a semi-rigid or stiff flex strap assembly 1 includes a first strap section 1A and a second strap section 1B. A coupling buckle 19 (e.g., rectangular buckle with two rectangular apertures bisected by a rigid body that runs perpendicular to the strap assembly from a center section of short ends of the rectangular coupling buckle 19) is coupled to one end of the second strap section 1B with an opposing end of the second strap section 1B coupled to a ratcheting buckle 3. The first strap section has a flexible portion 14 (see FIG. 3) and a semi-rigid portion 16 (see FIG. 3). One end of the flexible portion opposing another end abutting or coupled with the semi-rigid portion 16 (see FIG. 3) can be designated as a drawn end 12A (see FIG. 3) that is configured for feeding into and retraction within the ratcheting buckle 3. The semi-rigid portion 16 (shown in FIG. 3) is formed or configured to be at least partially fed into the coupling buckle 19 then folded over the coupling buckle 19 to fix the first strap section 1A with respect to the coupling buckle 19 and so can allow the ST assembly 11 to be configured into at least partially semi-rigid enclosing shape and applied with one hand in several modes. The flexible portion of the first strap section 1A is pre-positioned or pre-fed into the ratcheting buckle 3. The ratcheting buckle can be, e.g., a small ratchet with lightweight strong materials such as carbon composite materials. The coupling buckle 19 can be sized with larger apertures than the size of the semi-rigid portion 16 (shown in FIG. 3) of the first strap section 1A to permit easier insertion of the first strap section 1A by a wounded person. A user or injured party can manipulate or draw the semi-rigid portion 16 (shown in FIG. 3) of the first strap section 1A through the coupling buckle 19, bending the semi-rigid portion 16 (shown in FIG. 3) of first strap section 1A and wire 13 back over the coupling buckle 19 and undrawn first strap section 1A to form the ST assembly 11 into an enclosing structure then single handedly maneuvering the ST assembly 11 enclosing shape over an injured body section to a desired location between the person's heart and the injured section. Next, the user can commence ratcheting and drawing the flexible portion 14 (shown in FIG. 3) of the second strap section 1B using the ratcheting buckle 3 in order to place sufficient pressure on the body section in proximity to a wound area to reduce blood flow through the appendage.

An exemplary apparatus's strap section(s) can include a semi-rigid wire or wire ribbon or a wire or wires 13 formed into the first strap section 1A with a rubber grip coating 15 (see FIG. 3) on at least an end opposing an end connected to the ratcheting buckle 3. The exemplary apparatus ST assembly 11 can include a first medical module 2 (e.g., dual vitamin K auto injector and morphine auto injector in same case), a second medical module 6, e.g., a modal heart rate module coupled with embedded sensors in shirt (see FIG. 2) and/or a finger sensor pulse rate monitor 5 for redundancy, and the ratcheting buckle 3. The first medical module 2 can be configured with a delivery section, which can include a section that releases dual or individual injury treatment substances 35 (see FIG. 5) associated with treatment of one or more types of injury, e.g., vitamin K, which addresses or mitigates a particular injury (e.g., clots blood from an injury) or morphine for pain. One type of delivery mechanism can be a dual needle injection system (not shown) when applied or injected directly from medical module 2 or the first module 2 can be opened to allow individual removal and manual application of the injury treatment substance(s), e.g., vitamin K alone. A switch 41 (see FIG. 5) or delivery structure can include a syringe or a pressure container which pressure injects the individual injury treatment substances 35 (shown in FIG. 5) in combination or individually when pressed to the user's skin (or can be designed to inject through clothing).

Embodiments of the invention can be used to enable rapid one hand application/applied by injured patient to themselves including in situations where shock or injury has debilitated a user's cognitive functions thus increasing difficulty in using motor functions of their body to perform tasks. Embodiments can be configured to be ready for use and can be stored on a vest, on a strap embedded in pants lining or as heart rate sensors 4 (see FIG. 2) embedded into undershirt clothing of a user. An embodiment can include a timer 260 (see FIG. 10) and pulse monitoring 261 (see FIG. 10) section that respectively can provide time of ST 11 application and heart rate indication. The timer 260 (shown in FIG. 10) can be actuated by a switch, contact system, or other actuator including a switch built into the ratcheting buckle 3. An exemplary second medical module 6 can also be equipped with a transmitter/receiver, e.g., a system such as Bluetooth or another long-range system (e.g., Wi-Fi, cell phone system), for communicating with another communication system which is in turn connected with a remote medical monitoring by doctors in remote locations, not on-site. The second medical module 6 can further include a display showing information comprising date/time of activation of the ST 11 and heart rate information.

Figure 2:
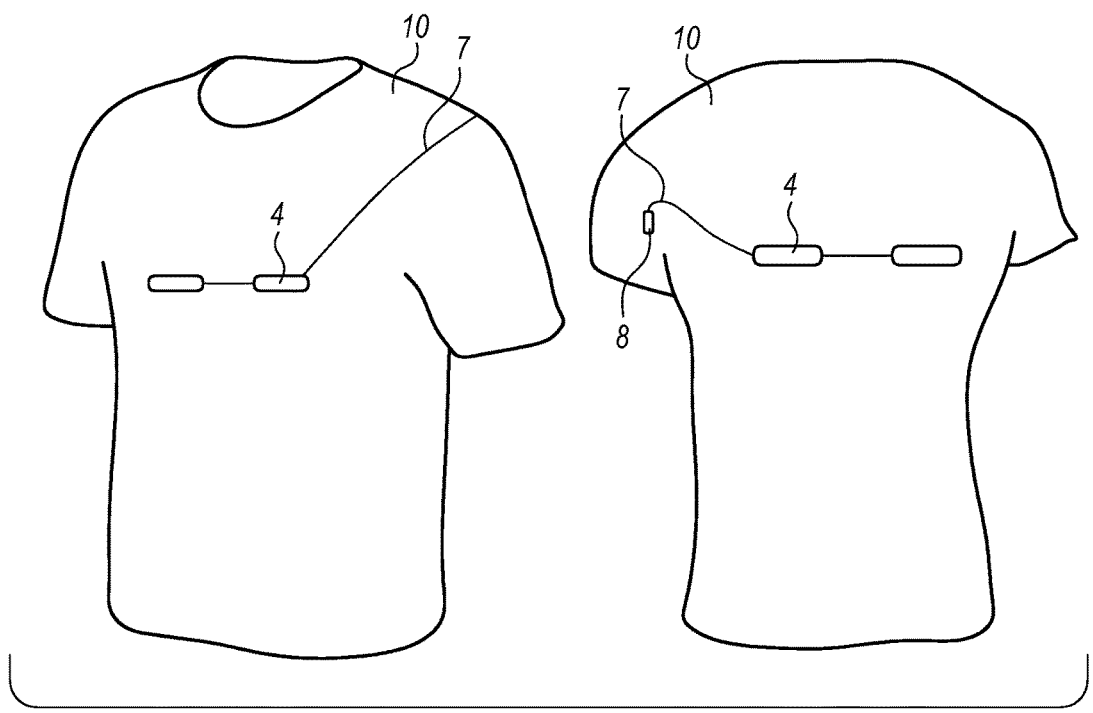
FIG. 2 shows an exemplary undershirt with built-in heart rate sensors and Universal Serial Bus (USB) connector in accordance with one embodiment of the invention.

FIG. 2 shows an exemplary undershirt 10 with built-in heart rate sensors 4 and USB connector 8 configured alongside a connecting wire 7 for detecting the user or casualty's heartbeat in accordance with one embodiment of the invention. The heart rate sensors 4 in the undershirt are positioned so they maintain constant contact with a user's skin and are positioned in proximity to the user's heart or upper chest region.

Figure 3A:
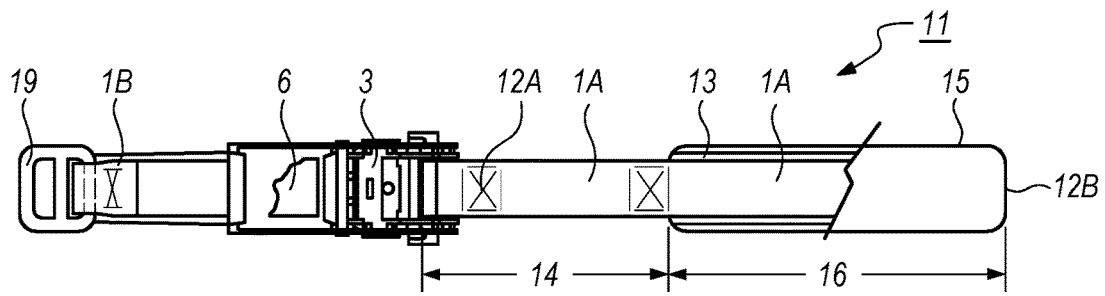
FIG. 3 shows a top and side view of the FIG. 1 ST's strap, ratchet, and an exemplary electronics module.
Figure 3B:
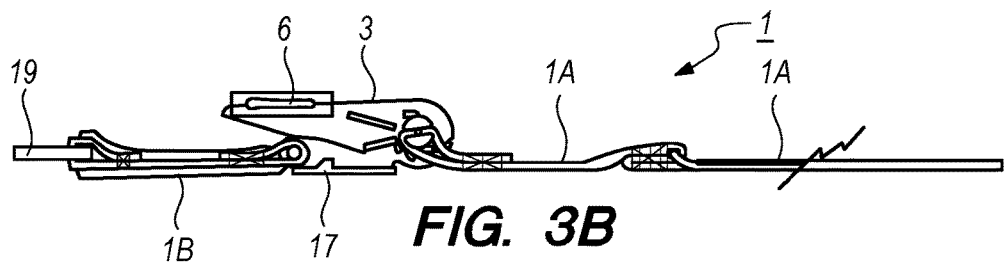

FIG. 3 shows top and side views of the FIG. 1 exemplary ST 11 construction including stitch joints, ratcheting buckle 3 with the second medical module 6 (shown in FIG. 1), e.g., electronics module that includes pulse monitor 261 (shown in FIG. 10) and transceiver (not shown), e.g., Bluetooth device. The first strap section 1A is formed with a flexible portion 14 and a semi-rigid portion 16 where the semi-rigid portion 16 includes a rubber grip coating 15 along with at least one embedded wire 13. The flexible portion 14 has a Drawn End 12A which is on an outer end of the overall first strap section 1A opposing a Fed End 12B defining an end section of the semi-rigid potion 16. The FIG. 3 diagram does not include the first medical module 2 in order to show more detail of the strap assembly 1. In this embodiment, the second strap section 1B is also coated with a rubber gripping material. The second strap section 1B is formed with a flexible material and has a different coupling buckle 19 which is formed into a rectangular shape with two rectangular apertures within it bisected by a structure running from a middle of the rectangular shape's ends defining the two rectangular apertures (first and second apertures). One end of the second strap section 1B is coupled through and with one of the two rectangular apertures (e.g. first aperture) and an opposing end of the second strap section 1B is fixedly coupled with the ratcheting buckle 3. A padding material 17 is shown underneath the ratcheting buckle 3 that is positioned to distribute force of the strap assembly 1 and ratcheting buckle 3 in order to reduce pressure point(s) applied to the user or casualty's appendage. The semi-rigid portion 16 of the first strap section 1A configured to be capable of being fed through the second aperture of coupling buckle 19, drawn through the second aperture of coupling buckle 19 and then folded over the coupling buckle 19 to fix the position of first strap section 1A with respect to the coupling buckle 19. The Fed End 12B is pre-fed or positioned into the ratcheting buckle 3 so that the ratcheting buckle 3 can rotate and draw the flexible portion 14 of the first strap section 1A into the ratcheting buckle 3 after the first strap section 1A has been fed through and folded over the coupling buckle 19.

Figure 4:
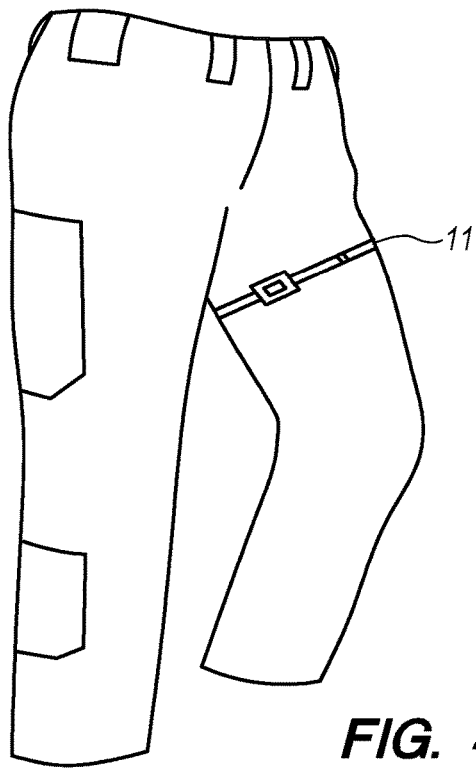
FIG. 4 shows an exemplary approximate location and application of an exemplary ST (e.g., see FIG. 1, FIG. 3) on an appendage such as a leg in accordance with one embodiment of the invention.

FIG. 4 shows an exemplary approximate location and application of an exemplary ST 11 (e.g., see FIGS. 1, 3) on a leg in accordance with one embodiment of the invention. This embodiment shows application of the ST 11 over a user's clothing.

Figure 5:
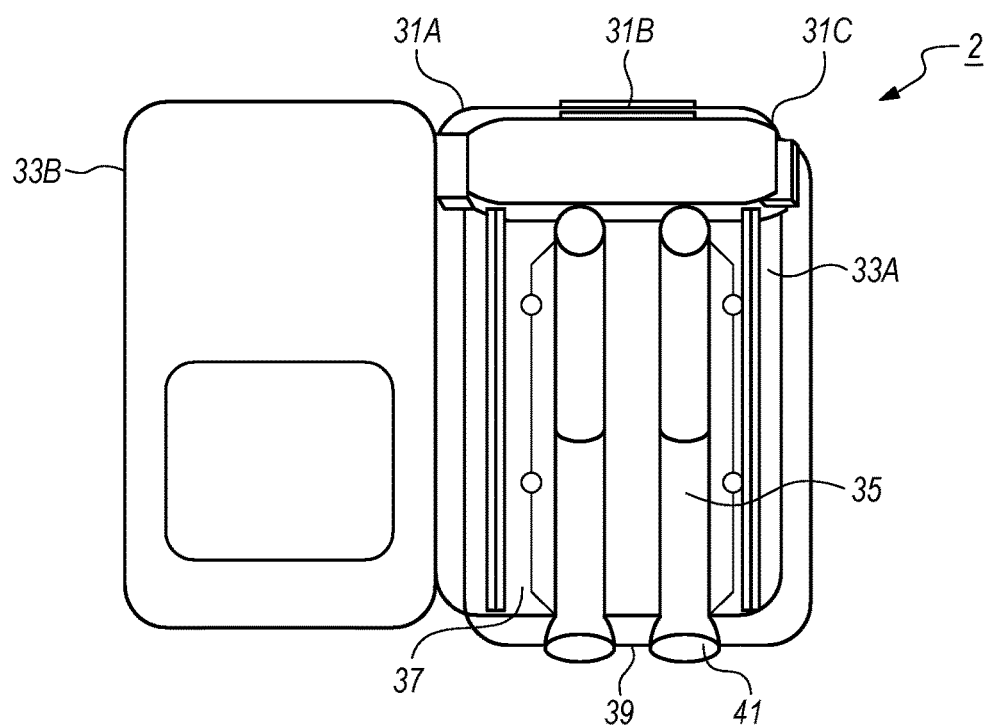
FIG. 5 shows a simplified drawing of an exemplary medical module.

FIG. 5 shows a drawing of an exemplary medical module 2 including individual injury treatment substance 35 for a vitamin K clotting agent, morphine, etc. The medical module 2 can include a selective single, dual, or multiple auto injector or manual injector and exemplary three button 31A, 31B, 31C safety features in accordance with one embodiment of the invention. When the exemplary three-button safety feature 31A, 31B, 31C are pressed at the same time and the medical module 2 with the switch 41 is applied with pressure to the injured area causes the injectors 35 to release vitamin K and morphine into the affected or injured area. This release of will induce necessary clotting of the injured party's blood in their wound and pain relief for the injured party. The lid 33B ensures the injectables are in a safe configuration prior to an injury while also allowing the injured party or casualty to be able to access the injectables when necessary. In one example, a clear cellophane covering seal 39 covers the injectables as an additional layer of protection; the casualty can apply the injectables while pressing the three button safety features 31A, 31B, 31C of medical module 2 in order to cause needles (not shown) to puncture the seal 39 when activated.

Figure 6:
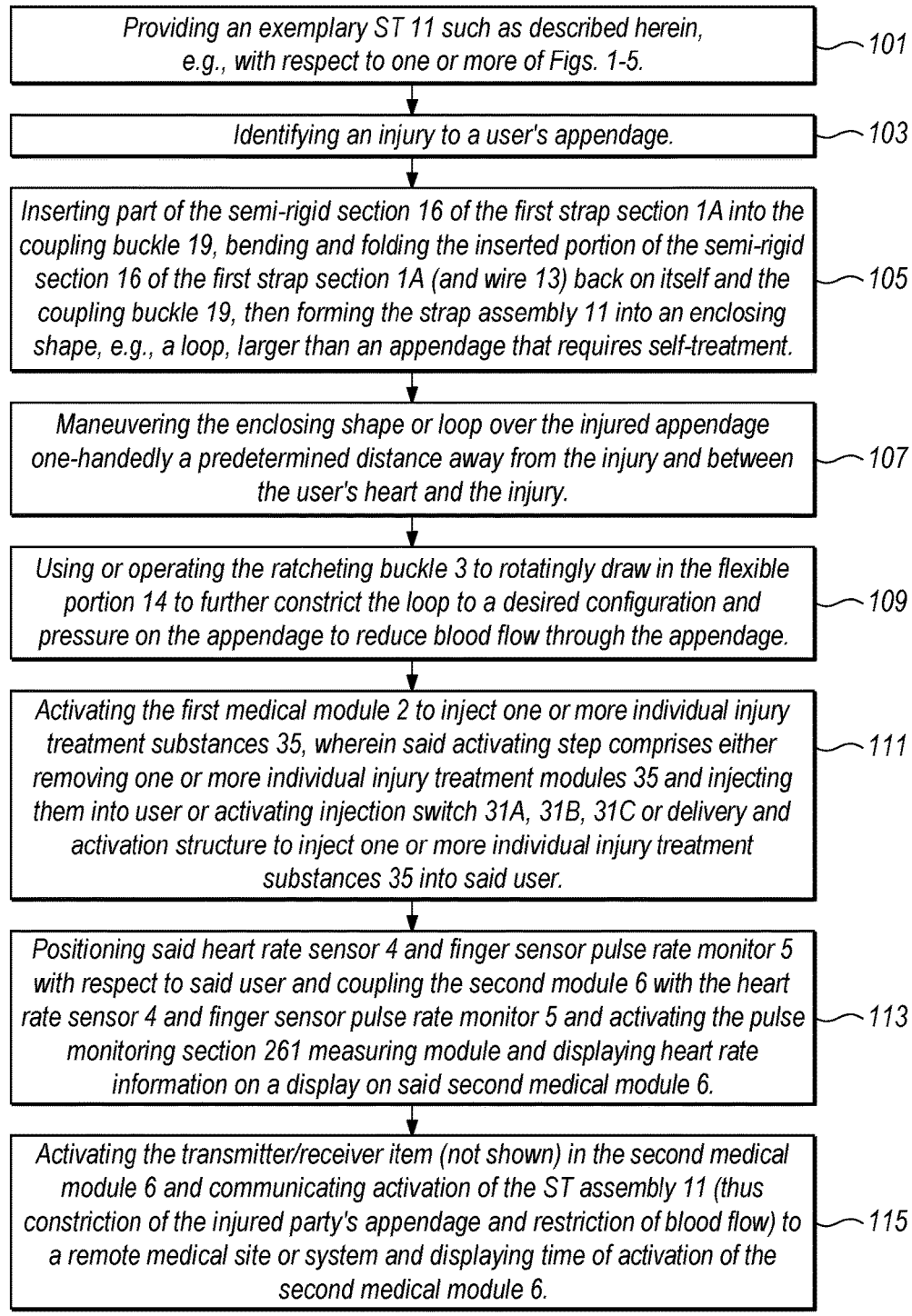
FIG. 6 shows a method of using an exemplary embodiment of the invention (e.g., shown at one or more of FIGS. 1-5)

FIG. 6 shows a method of using an exemplary embodiment of the invention. Referring to FIG. 6, a method of operation can include: Step 101: providing an exemplary ST 11 such as described herein, e.g., with respect to one or more of FIGS. 1-5. At Step 103: Identifying an injury to a user's appendage. At Step 105: Referring to FIG. 3, inserting part of the semi-rigid section 16 of the first strap section 1A into the coupling buckle 19, bending and folding the inserted portion of the semi-rigid section 16 of the first strap section 1A (and wire 13) back on itself and the coupling buckle 19, then forming the strap assembly 1 into an enclosing shape, e.g., a loop, larger than an appendage that requires self-treatment. At Step 107: maneuvering the enclosing shape or loop over the injured appendage one-handedly a predetermined distance away from the injury and between the user's heart and the injury. At Step 109: using or operating the ratcheting buckle 3 to rotatingly draw in the flexible portion 14 to further constrict the loop to a desired configuration and pressure on the appendage to reduce blood flow through the appendage. At Step 111: Referring to FIG. 5, activating the first medical module 2 to inject one or more individual injury treatment substances 35, wherein said activating step comprises either removing one or more individual injury treatment modules 35 and injecting them into user or activating injection switch 31A, 31B, 31C or delivery and activation structure to inject one or more individual injury treatment substances 35 into said user. Step 113: positioning said heart rate sensor 4 and finger sensor pulse rate monitor 5 with respect to said user and coupling the second module 6 with the heart rate sensor 4 and finger sensor pulse rate monitor 5 and activating the pulse monitoring section 261 (shown in FIG. 10) measuring module and displaying heart rate information on a display on said second medical module 6. At Step 115: activating the transmitter/receiver item (not shown) in the second medical module 6 and communicating activation of the ST assembly 11 (thus constriction of the injured party's appendage and restriction of blood flow) to a remote medical site or system and displaying time of activation of the second medical module 6.

Figure 7:
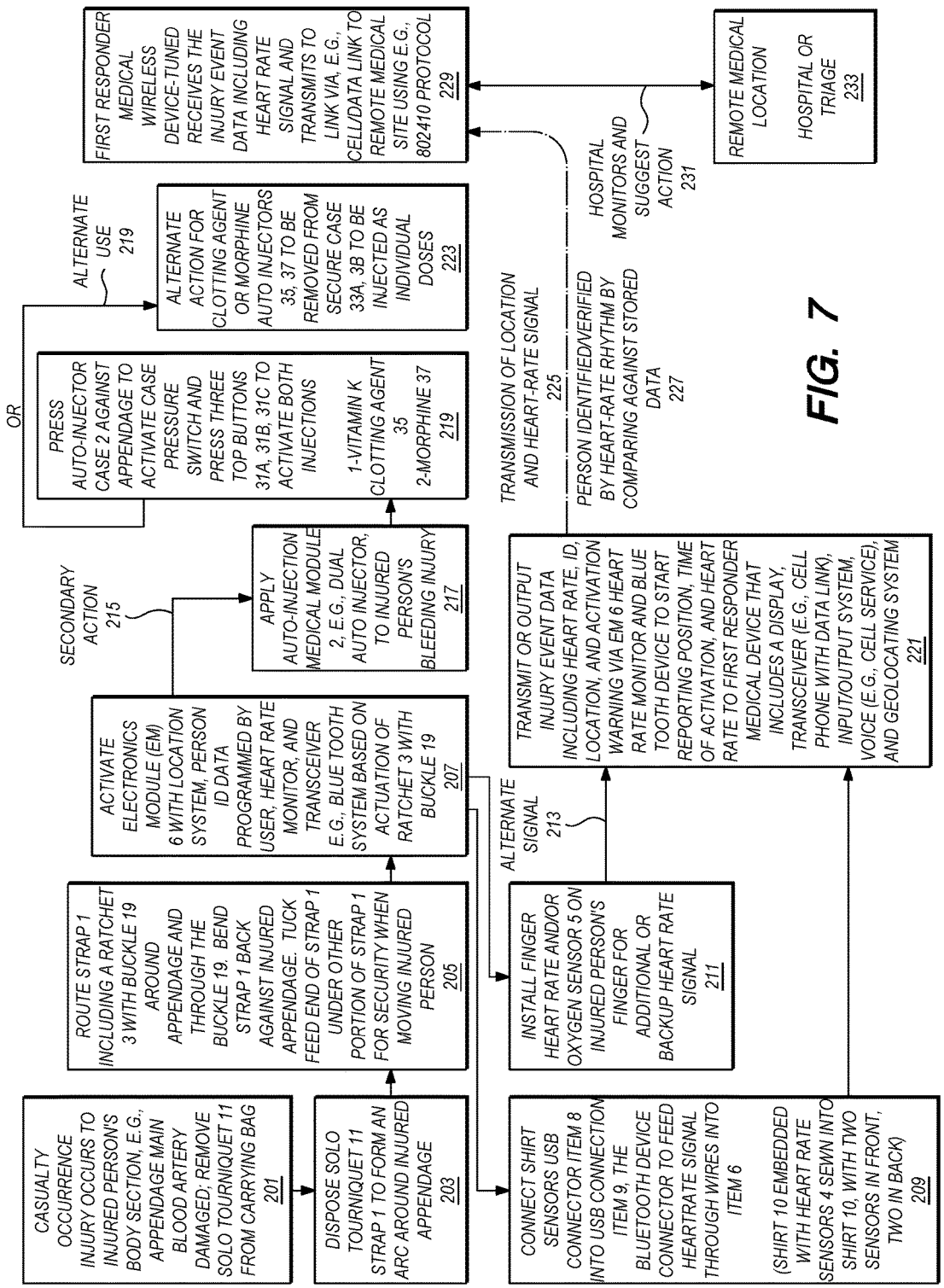
FIG. 7 shows another method in accordance with another exemplary embodiment of the invention.

FIG. 7 shows another method in accordance with another exemplary embodiment of the invention. The embodiment illustrates what the ST 11 and first medical module 2 can do when a casualty occurs. At step 201, a casualty occurrence event occurs to a person's body section, e.g., an appendage's artery. At step 203, manipulating or forming ST 11 strap assembly 1 to form an enclosing shape, e.g., an arc or circular shape, around injured appendage. At step 205, route strap assembly 1 including a ratcheting buckle 3 with coupling buckle 19 around injured appendage 203 and through the coupling buckle 19 to a position between the injury and the person or user's heart; bend strap assembly 1 (e.g., semi-rigid portion 16 of strap assembly section 1A) back against injured appendage. Tuck and feed or fold over an unfed section of strap assembly 1 (an unfed section of semi-rigid portion 16) under another portion of strap assembly 1 for security when moving injured person. At Step 217: activate second medical module 6 with location system 263 (see FIG. 10), person ID 262 (see FIG. 10) data programmed by user, heart rate monitor 261 (shown in FIG. 10), and transceiver (not shown) e.g., Bluetooth system based on actuation of ratcheting buckle 3 with coupling buckle 19. After step 207, at Step 209: coupling a connected shirt sensors 4 USB connector 8 into USB connection 9 and/or use of the Bluetooth device connector to feed heart-rate signal through wires into second medical module 6. Optionally, at Step 211, an alternative option can employ finger sensor pulse rate monitor 5 on the injured person's finger for additional or backup heart rate signal. At Step 221, pulse rate monitor 5 and/or the signal from the shirt sensors will transmit/output injury event data including pulse monitoring section 261, person ID 262, location 263, and activation warning via second medical module 6, heart rate monitor 4, and Bluetooth device (not shown) to start reporting position, timer 260 and heart rate to first responder medical device that includes a display transceiver (e.g. cell phone with data link), input output system, voice (e.g. cell service), and geo-locating system. At Step 225, transmission of location and heart rate signal, person identified/verified by heart-rate rhythm by comparing against stored data is executed. At step 229, a first responder medical wireless device 253 (see FIG. 8) receives the injury event data including heart rate signal then the first responder medical wireless device 253 transmits the injury event data via e.g., cell/data link to remote medical site using a transmission data protocol, e.g. 802410 protocol. At step 231, hospital staff remotely monitors the transmitted injury event data then the hospital staff suggests action to user or operator of the first responder wireless medical device 253. At Step 217, a secondary or parallel action can include applying auto injection from first medical module 2, e.g. dual auto injector, to injured an person's injury area. Two alternative options can be provided for at Steps 219 (activation within case) or 233 (removal of injectors from case and separate manual activation). In particular, at Step 219, pressing the auto injector case from first medical module 2 against the injured appendage to activate case pressure switch and pressing the three top buttons 31A, 31B, 31C to activate multiple injections, e.g. vitamin K clotting agent and morphine. At Step 223, alternatively, a process can include applying the clotting agent or morphine auto injectors from individual injury treatment substance 35 removed from secure case 33A and injected as individual doses.

Figure 8:
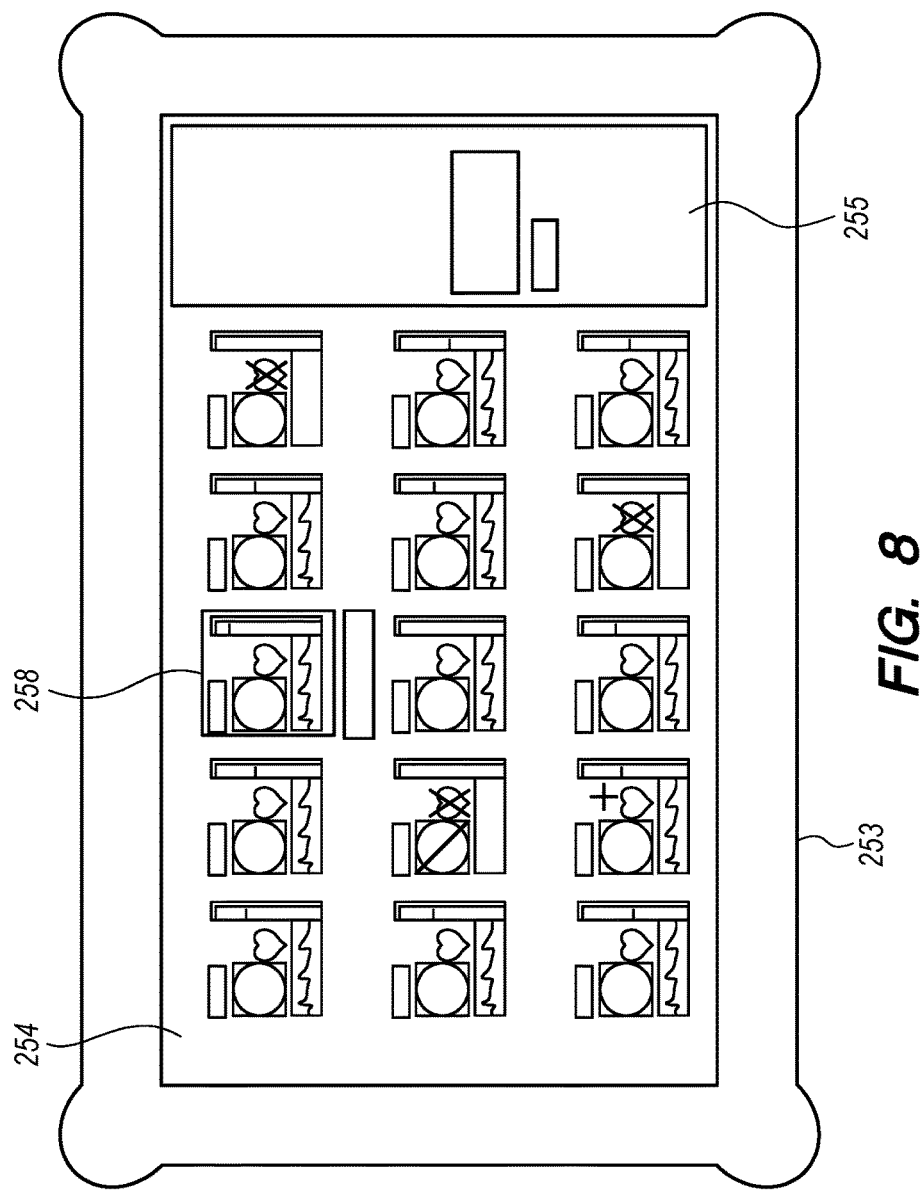
FIG. 8 shows a medical wireless device configured to communicate with an embodiment of the ST's electronic module that includes a display and an exemplary graphical user interface (GUI) shown in the display in accordance with one exemplary embodiment of the invention.

FIG. 8 shows a medical wireless device 253, e.g. a ruggedized tablet computer with, one or more interfaces including a touch screen interface 254 configured to display a plurality of GUI's 258 showing activation status (see FIG. 10, 260), signal status (FIG. 10, 259), personal medical information (FIG. 10, 255), medical treatment and related data, evacuation status, response team pickup location, and bearing to patient location 263 (shown in FIG. 10), configured to communicate with a remote site and various components, e.g., an electronics module, in accordance with one exemplary embodiment of the invention.

Figure 9:
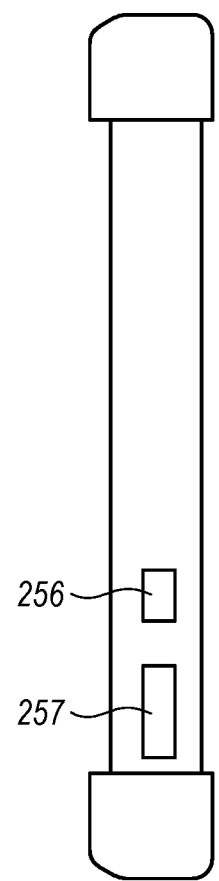
FIG. 9 shows a side view of the FIG. 8 medical wireless device.

FIG. 9 shows a side view of the FIG. 8 medical wireless device 253. A side view of the medical wireless device 253 comprises a power plug receiver 256 to provide power to the medical wireless device 253 and also a USB port 257 that can be used for a multitude of functions, e.g., provide connection for the medical wireless device 253 to a computer system.

Figure 10:
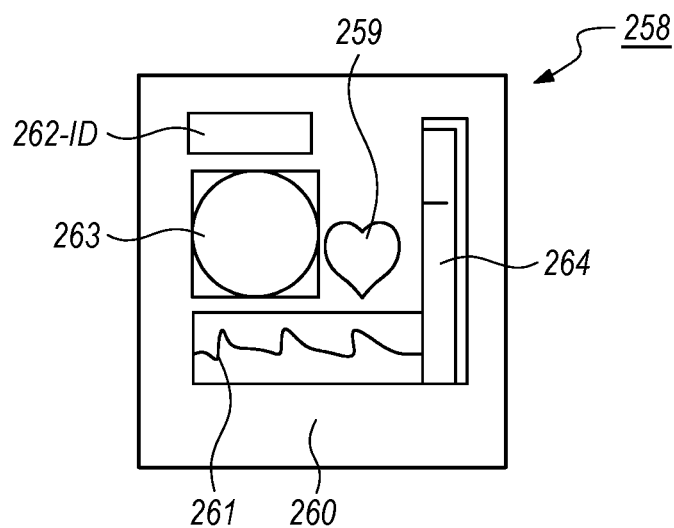
FIG. 10 shows a detail view of one GUI element from the FIG. 8 medical wireless device and display.

FIG. 10 shows a detail view of one GUI element from the FIG. 8 medical wireless device 253 and its touch screen interface 254. GUI 258 displayed on the touch screen interface 254 in the medical wireless device 253 and is comprised of a thermal range indicator 264 that will indicate the basal body temperature of the casualty, a relative position indication 263 that will allow a first responder, e.g., a person coming to assistance of a casualty, to locate the casualty faster, a pulse rate monitoring section 261 that would allow the individual heading to the casualty to be able to monitor the said casualties pulse; a signal strength indicator displayed as a heart 259; this heart will indicate to the person with the medical wireless device looking at said casualty's GUI the strength of the signal to the said casualty; an ID indicator 262 of the casualty, this will aid the medic in identifying which casualty applied the ST 11 in the field; and an applied time indicator 260 that will allow the medic to have an accurate account of time the ST 11 has been applied to the casual.

Figure 11:
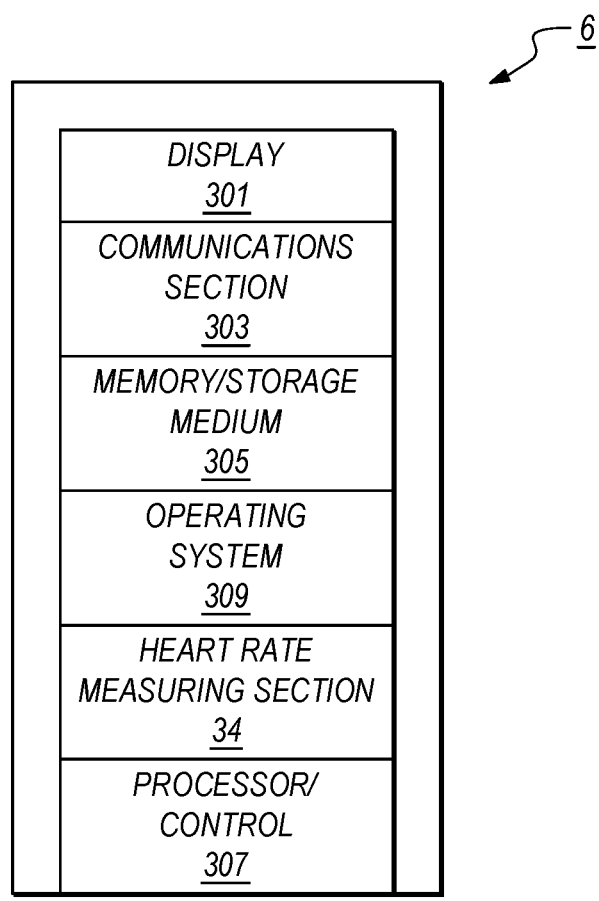
FIG. 11 shows processing components of the GUI.

FIG. 11 shows an exemplary functional block diagram for a second medical module 6. FIG. 11 shows a touch screen and display 301, communications module 303, a memory/storage medium 305 and a processor/controller 307. A computer or device operating system 309 is stored on the memory/storage medium 305. The second medical module 6 also can include a heart rate measuring module 34. The heart rate measuring module 34 can be hardwired or a software system loaded on the memory/storage medium 305. The operating system 309 can include e.g. Darwin, RTXC, LINUX, UNIX, OS X, WINDOWS, or an embedded operating system such as VxWorks and can include various software components and/or drivers for controlling and managing general system tasks (e.g., memory management, storage device control, power management, etc.) and facilities communication between various hardware and software components. The processor/controller 307 executes instructions from, e.g., the operating system 309 and various system components or software programs including ones such described herein. The touch screen and display 301 shows user identification information, heart rate, whether the medical module 6 is operating effectively, duration of activation, and body temperature. The communication module 303 facilitates communication with other devices over one or more external ports via an input/output module and also includes various software components for handling data that communicate with the finger sensor pulse rate monitor 5 and embedded shirt heart rate sensors 4 for direct communication to the second medical module 6. The communication module 303 also communicates with the medical wireless device 253.

Although the invention has been described in detail with reference to certain preferred embodiments, variations and modifications exist within the spirit and scope of the invention as described and defined in the following claims.

The invention claimed is:

1. A self-treatment medical apparatus comprising:
a strap assembly (SA) including a first and second strap section, said first strap section comprises a flexible or semi-rigid structure with a non-slip coating;
a buckle coupled with a first side of said second strap section, said buckle configured to receive a first end of said first strap section with a non-interference fit;
a selectively lockable ratchet rotatably coupled with a second end of said second strap section and configured to rotatably draw in said second strap section;
a first medical module coupled with said strap assembly comprising a case and at least one injury treatment substance injection module disposed within the case; and
a second medical module comprising a heart rate monitor, a display, an activation switch section, a memory, a transmitter/receiver comprising a near or longer range system, wherein the second module further includes a display showing information comprising, casualty location, date/time of activation of the self-treatment medical apparatus and heart rate information and a controller or processor, coupled with the strap assembly, wherein said controller or processor is configured with a timer section configured to receive an input from the activation switch section and display a time since application of the self-treatment medical apparatus.

2. An apparatus as in claim 1, wherein said near or longer range system is configured to be operable for communicating with another communication system which is in turn connected with a remote medical monitoring system used by doctors in remote locations.

3. A method of use of a medical device embodiment comprising:
providing a self-treatment medical apparatus comprising:
a strap assembly including a first and second strap section, said first strap section comprises a flexible semi-rigid structure adapted to be bendable and retain its position after bending up to a first force, said first strap section comprises a non-slip coating;
a buckle coupled with a first side of said second strap section, said buckle configured to receive a first end of said first strap section with a non-interference fit;
a selectively lockable ratchet rotatably coupled with a second end of said second strap section and configured to rotatably draw in said second strap section;
a first medical module coupled with said strap assembly comprising a case and at least one injury treatment substance injection module disposed within the case; and
a second medical module comprising a heart rate monitor, a display, an activation switch section, a memory, a transmitter/receiver comprising a near or longer range system, wherein the second module further includes a display showing a plurality of injury event data generated by said second medical module comprising heart rate, medical module or user identification data, location, and activation warning transmitted via said receiver/transmitter configured to start reporting position, time of activation, heart rate, and medical device location, and date/time of activation of the medical device, said second medical module further comprising a controller or processor, coupled with the strap assembly, wherein said controller or processor is configured with a timer section configured to receive an input from the activation switch section and display a time since application of the self-treatment medical apparatus, said second medical module further comprises an activation switch coupled with said ratchet configured to activate said second medical module;

manipulating the strap assembly strap to form said first and second strap sections into an arc or surrounding structure that is then moved around an injured appendage so as said strap assembly strap is positioned between an injury section of said injured appendage and the user's heart then feeding said first strap section through said buckle and bending to draw said strap assembly strap into contact with said injured appendage and then bending said first strap section outside of said buckle back onto said strap assembly strap; and activating said second medical module based on actuation of said activation switch in said ratchet.

4. A solo tourniquet (ST) device strap assembly apparatus comprising:

a flexible strap section having a ratcheting strap retraction unit or buckle coupled to one end of the first flexible strap section and an oversized buckle on an opposing end of the first strap section;

a second strap section formed with a flexible portion as well as a semi-rigid portion where the flexible portion of the second strap section is pre-fed into the ratcheting strap retraction unit or buckle, wherein the semi-rigid portion is adapted to be insertable into an aperture in the oversized buckle and drawn through the aperture until ST device is configured into an enclosing shape, wherein the ratcheting strap retraction unit or buckle is further configured to draw the pre-inserted second strap section into the ratcheting strap section to apply enclosing pressure to the injured appendage;

an injector medical case module, a medical condition monitoring system that can also include a remote monitoring system including a transmitter and receiver, a heart monitor attached to finger sensor, and embedded shirt heart rate sensors;

an injury mitigation medication system configured to pressure inject medical treatments into a casualty or user's body section in proximity to one side of the injury mitigation medical system comprising a blood clotting agent, wherein the injury mitigation medical system further comprises a fluid injection selection safety switch and injection system, the injury mitigation medical system further comprises a medical wireless device, a geolocation system, a timer, a display, a transmitter/receiver, and activation section.

5. An apparatus as in claim 4, wherein said transmitter/receiver is a cellular phone.

6. An apparatus as in claim 4, wherein the medical wireless device has one or more interfaces including a touch screen interface configured to display a plurality of graphical user interfaces (GUI) showing activation status, signal status, vital signs, personal medical information, medical treatment, and related data, evacuation status, response team pickup location, and bearing to the casualty or user's location.

7. An apparatus as in claim 4, wherein the medical wireless device comprises a power supply coupling section and a USB port configured to provide connection for the medical wireless device to a computer system.

8. An apparatus as in claim 4, wherein the GUI on the medical wireless device is comprised of:

a thermal range indicator configured to indicate a basal body temperature of the casualty or user;

a position location screen configured to show a present location and a direction or location of the geolocation system configured to guide an operator of the GUI to a location of the casualty or user faster;

a pulse rate monitor that configured to monitor and display the said casualty's pulse;

a signal strength indicator showing a detected signal strength of the transmitter;

an identifier or ID indicator of said casualty, said ID indicator configured for identifying an identifier to the user or casualty and use of the medical; and an applied time indicator showing a date and time apparatus has been applied to the casualty or user.

* * * * *